United States Patent [19]

Hosoda et al.

[11] Patent Number: 5,034,006
[45] Date of Patent: Jul. 23, 1991

[54] SUCTION EQUIPMENT FOR MEDICAL OPERATION

[75] Inventors: Yasuyuki Hosoda, Hino; Kazunori Kudo, Tokyo; Toshio Izumi, Kawanishi, all of Japan

[73] Assignee: Takeda Chemical Industries, Ltd., Osaka, Japan

[21] Appl. No.: 489,727

[22] Filed: Feb. 28, 1990

Related U.S. Application Data

[63] Continuation of Ser. No. 208,126, Jun. 17, 1988, abandoned.

[30] Foreign Application Priority Data

Jun. 22, 1987 [JP] Japan ................. 62-154813

[51] Int. Cl.$^5$ ................. A61M 1/00; A61F 7/00
[52] U.S. Cl. ................. 604/317; 604/268; 604/356; 128/400; 128/402
[58] Field of Search ................. 604/27, 30–35, 604/39, 43, 45, 73, 113, 264, 268, 289, 291, 313, 315, 317, 356, 357, 266; 600/37; 128/65, 66, 399, 400, 402, 403, 850

[56] References Cited

U.S. PATENT DOCUMENTS

| | | | |
|---|---|---|---|
| 3,421,510 | 1/1969 | Kettenbach | 604/45 |
| 3,674,031 | 7/1972 | Weiche | 128/400 |
| 3,823,720 | 7/1974 | Tribble | 604/43 |
| 4,154,245 | 5/1979 | Daily | 128/400 |
| 4,217,904 | 8/1980 | Zahorsky | 604/268 |
| 4,259,961 | 4/1981 | Hood, III | 128/400 |
| 4,508,533 | 4/1985 | Abramson | 604/45 |
| 4,533,352 | 8/1985 | Van Beek et al. | 604/317 |
| 4,579,555 | 4/1986 | Russo | 604/266 |

*Primary Examiner*—John D. Yasko
*Assistant Examiner*—Anthony Gutowski
*Attorney, Agent, or Firm*—Wenderoth, Lind & Ponack

[57] ABSTRACT

Auxiliary suction equipment for performing a medical operation. A flexible mat partitions off an organ to be operated on from other internal organs, and a suction tube removes blood and body fluid caused by the operation. The insulating qualities of the mat allow the procedure to be performed with the protection of the organ muscle by a local low-temperature method in order to control the metabolism of the organ to be operated on. The mat can be provided with a passage to introduce a fluid for controlling the temperature of the mat surface.

9 Claims, 4 Drawing Sheets

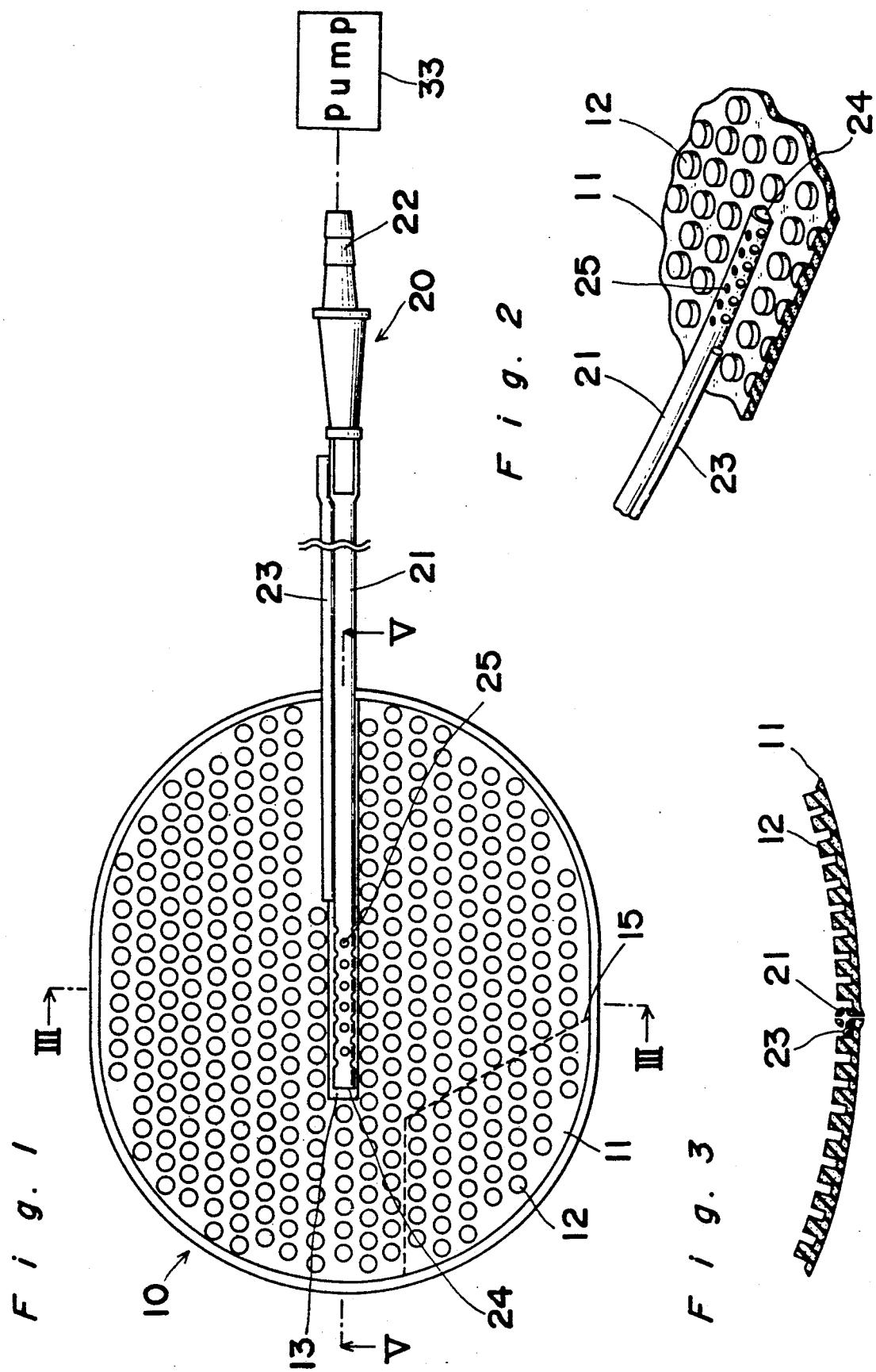

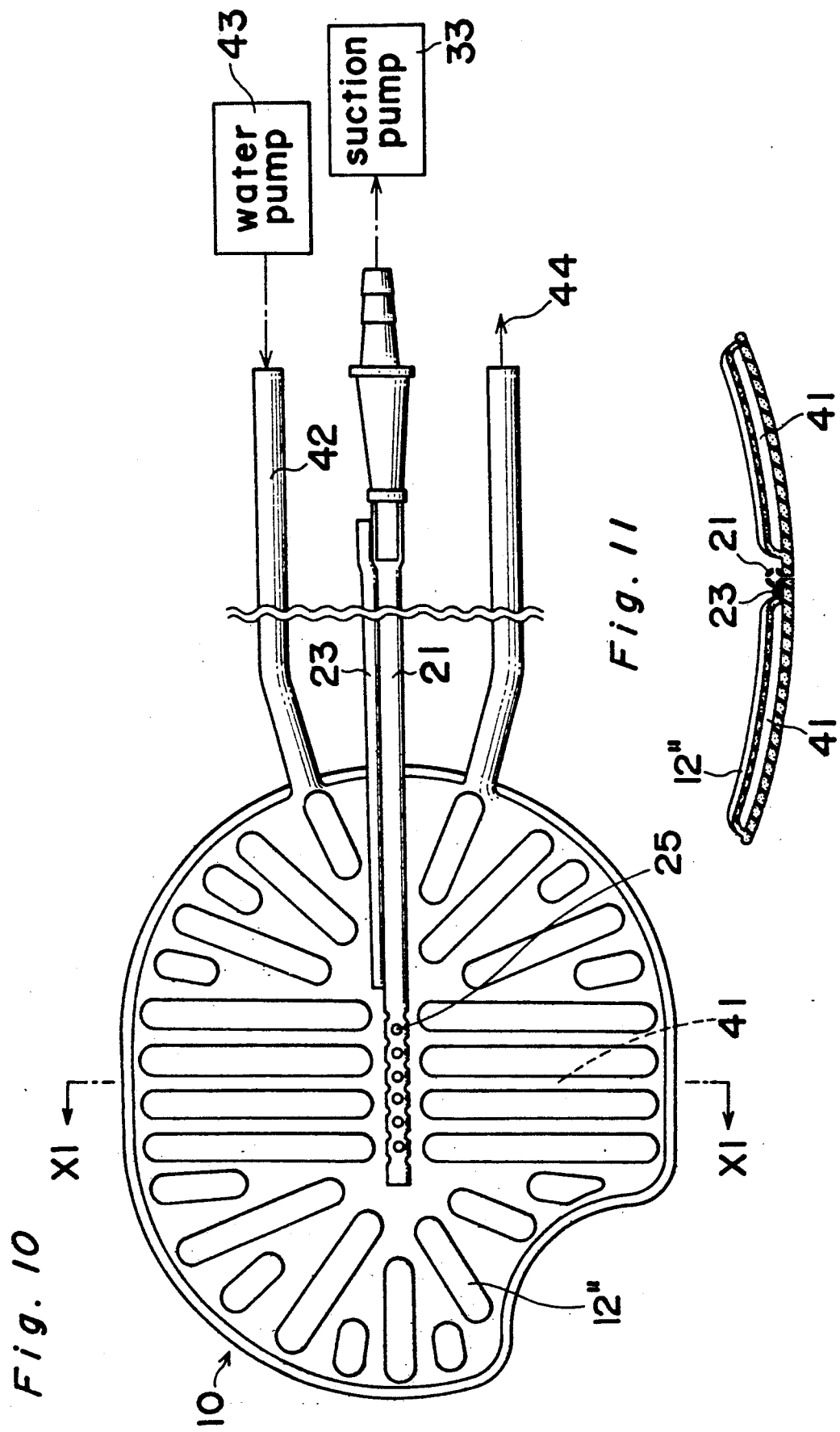

SUCTION EQUIPMENT FOR MEDICAL OPERATION

This application is a continuation of now abandoned application, Ser. No. 07/208,126 filed on June 17, 1988, abandoned.

BACKGROUND OF THE INVENTION

The present invention generally relates to auxiliary suction equipment for performing a medical operation such as a heart operation, a liver operation, and an orthopedic surgery to cause blood to issue from an organ.

To facilitate understanding of the present invention the following explanation, proceeds in connection with a medical operation especially related to a heart operation. For instance, the present invention is to provide auxiliary suction equipment for use in a heart operation which partitions off a heart, and cooling ice-slushes from other internal organs, absorbs, removes blood, body fluid caused from the operation and thawed water or the like from the ice slush in a heart operation performed will protection of the heart muscle by a local low-temperature method in order to control the metabolism of the heart to be operated on. Such an operation is performed simultaneously with the use of an ectosomatic auxiliary circulating circuit or a cardiovascular system which temporarily performs the pump operation of the heart in the mechanical way.

Generally, in order to partition off a heart or the like from the other internal organs, doctors cut blister polyurethane or silicone resin sheet into the proper size with a pair of scissors to wrap the heart or the like or insert gauze, etc. thereinto if necessary. Also, various shapes of spreader sets or suckers were commonly used for absorbing blood, body fluid ice slush, etc. caused during the operation to re-use or remove it, with one assistant being required for the operation thereof.

SUMMARY OF THE INVENTION

Accordingly, an essential object of the present invention is to provide novel auxiliary suction equipment which is capable of carrying out a medical opening procedure using an ectosomatic auxiliary circulating circuit or a cardiovascular system without hindrance, and which is easy to operate and simple in construction.

One consideration in the invention is that sufficient adiabatic effect is obtained with the employment of plastic materials for a base plate of a mat means so that adjacent diaphragm nerve will not be paralyzed. The mat means is made of soft plastic which is highly flexible and is deformed to suit the shape of the heart. Blood or fluid from the heart or the like naturally flows into suction openings of a tube provided on the mat means. The shape and size of the base plate may be easily changed with scissors in accordance with the heart size, the neighboring internal organ condition and the need to keep the suction openings of the tube from being closed by the internal organs. The construction of the suction equipment may be simple and low cost.

According to the present invention, the suction equipment for use in a medical operation comprises a mat means made of soft molded plastic and includes a thin partition plate with enough thickness to maintain a given shape so as to suit the shape of an organism such as a human heart with enough area to wrap the portion of the organ of interest. A plurality of projections are distributed on at least the upper surface of the partition plate, with a height to allow flow fluid thereamong, and a suction means including a flexible tube whose one end is mounted on the upper surface of the partition plate. The tube has an opening for introducing liquid from the base plate into the tube, and an other end extending out of the partition plate has a connector for connecting with a pump which is operated to remove the liquid from the partition plate through the tube.

The partition plate of the mat means is inserted between the operating portion, such as a heart to be operated on, and the other internal organs, with refrigerants such as ice slushes being thrown between the mat means and the heart. The connector at the other end of the tube is connected with the suction opening of a pump. Body fluid, blood or the like from the organ during the operation gathers into the suction openings of the tube along the flow path of the surface of the base plate, so that it is absorbed, re-used or removed.

BRIEF DESCRIPTION OF THE DRAWINGS

These and other objects and features of the present invention will become clear from the following description taken in conjunction with the preferred embodiments thereof with reference to the accompanying drawings, in which:

FIG. 1 is a top view of a first embodiment of the present invention;

FIG. 2 is a perspective view, on an enlarged scale, of a central portion of FIG. 1;

FIG. 3 is a cross-sectional view taken along a line III—III of FIG. 1;

FIG. 10 is a top view of a fourth embodiment of the present invention,

FIG. 11 is a cross-sectional view taken along a line XI—XI of FIG. 10.

DETAILED DESCRIPTION OF THE INVENTION

Figure 5:
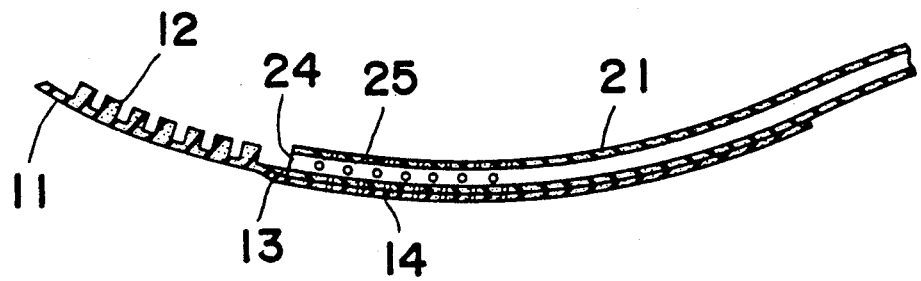
FIG. 5 is a cross-sectional view taken along a line V—V of FIG. 1.

Before the description of the present invention proceeds, it is to be noted that like parts are designated by like reference numerals throughout the accompanying drawings. Also, the following description proceeds by way of example for an application to a heart operation on a human being.

FIGS. 1 to 5 show a suction equipment for use in medical operation in accordance with a first embodiment of the present invention, which can easily partition off a portion of an organ such as a heart, to be operated on from other internal organs. In a heart opening the protection of the heart is by a local low-temperature method of controlling the metabolism of the patient with the simultaneous use of an ectosomatic auxiliary circulating circuit, which performs the pump operation of an auxiliary agency for the heart in a mechanical way.

Referring to FIG. 1, the suction equipment comprises a mat means 10 including a pan-type partition plate 11 to be placed in the space between the heart to be operated on and other internal organs. A plurality of projections 12 are provided on the partition plate 11 to form passages from flowing blood or body fluid generated from the parts of the patient operated upon. The passages connect the entire area of the partition plate 11 to the central portion of the partition plate 11. A suction means 20 includes a suction tube 21, one end of which is open at the central portion of the partition plate 11 while the other end is connected to a suction pump 33 through a connector 22, in order to remove the blood or body fluid from the central portion of the partition plate 11 to the suction pump 33. An and air tube 23 introduces air from the outside of the partition plate 11 to the neighborhood of an opening 24 of the suction tube 21.

Figure 4:
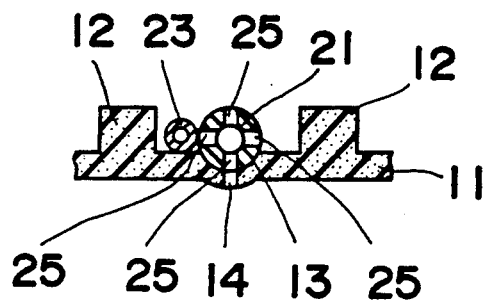
FIG. 4 is an enlarged cross-sectional view of a central portion of FIG. 2.
Figure 8:
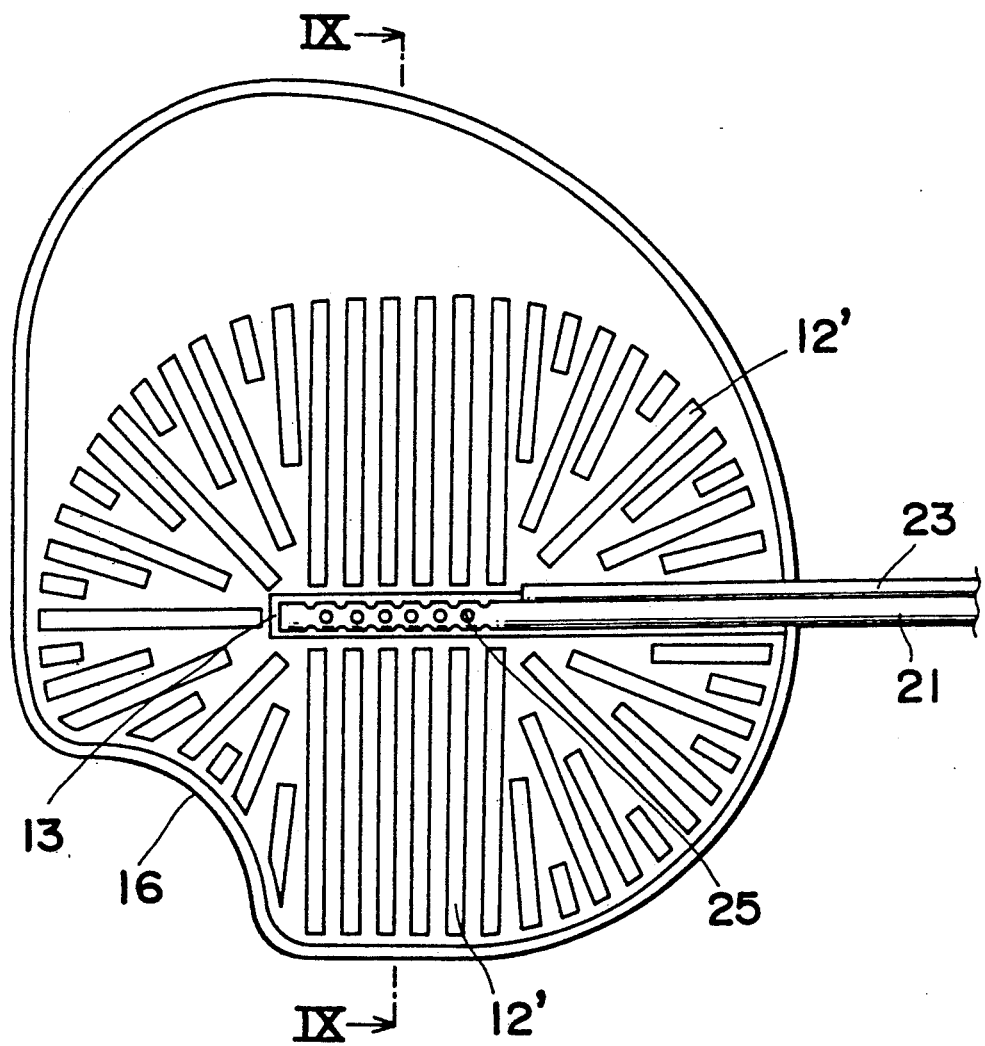
FIG. 8 is a top view of a third embodiment of the present invention.
Figure 9:
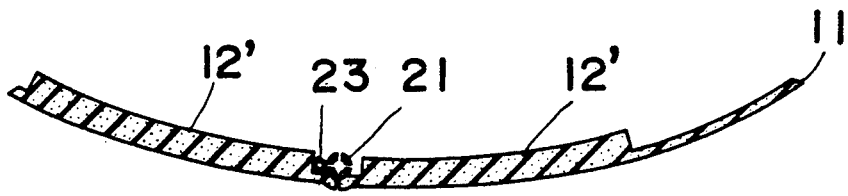
FIG. 9 is a cross-sectional view taken along a line IX—IX of FIG. 8.

The partition plate 11 has a size large enough to wrap half of the heart, with the long diameter being 120 mm and, the short diameter being 100 mm. The small projections 12 arranged on the plate are each 2 through 5 in height and 1 through 2 mm in thickness. The partition plate 11 is curved like a round plate, and is flexible so that it may be freely deformed through application of small amount of force. The shape of the small projections 12 is such that a continuous flow route is formed, as by dot-shape 12 with a diameter of 3 to 5 mm and a height of 2 to 4 mm, as shown in FIG. 4, by linear shape 12' with a length of more than 5 mm and a height of 3 mm, as shown in FIG. 8, or by other shapes. The tops of the projections 12 are formed with flat surfaces so as to abut smoothly with the heart of the patient to be treated.

Figure 6:
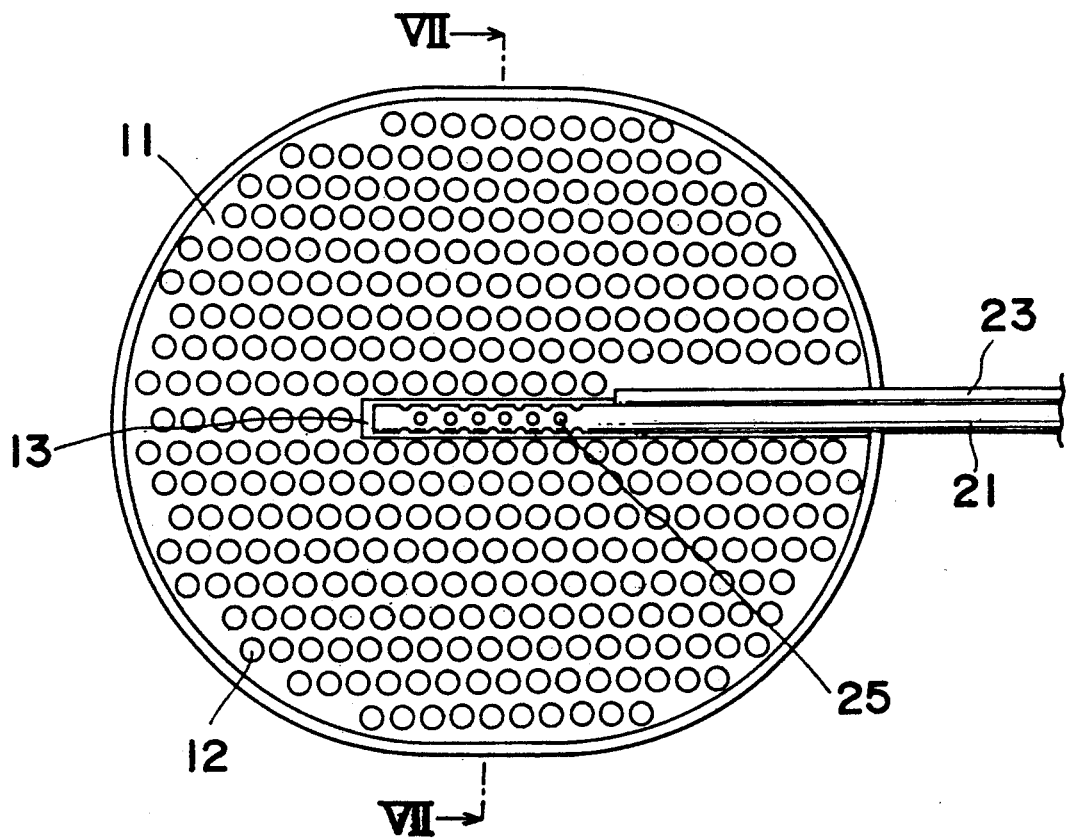
FIG. 6 is a top view of a second embodiment of the present invention.
Figure 7:
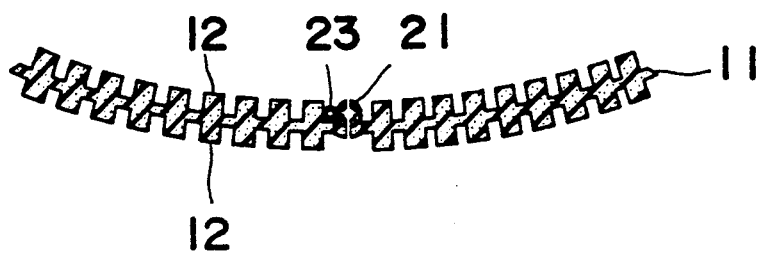
FIG. 7 is a cross-sectional view taken along a line VII—VII of FIG. 6.

Also, the arrangement of projections 12 is not restricted to the front face of the partition plate 11, but may be provided on the back face of the partition plate 11 as well, as shown in FIGS. 6, 7 of the second embodiment of the invention. The projections 12 provide a thermal insulating function for the partition plate 11 and a passage forming function for liquid to be sucked by the suction tube 21.

The partition plate 11 with projections 12 is integrally molded of plastic, such as soft plastic, foamed plastic or the like. The plastic should be flexible, adiabatic even at low temperatures of 0° trough 4° C, and adapted as a thermal insulating material. Typical materials include silicone, polyethylene, urethane, vinyl chloride or blister materials thereof, with blister material of silicone-origin resin being desirable. In addition, the partition plate 11 is provided with a line of perforations 15 to tear off some portion of the partition plate 11 to optionally reduce the area of the partition plate 11 in order to fit to the size of the heart to be treated.

The suction tube 21, made of transparent soft plastic, has an outer diameter of 4 mm and an inner diameter of 2.5 mm. Suction opening 24 is provided in one end portion thereof to receive the fluid, and a connector 22 is provided in the other end thereof for connection with a suction pump 33. The end portion with opening 24 is bonded by a bonding agent within a groove or concave 13 provided at the central portion of the front surface of the partition plate 11. The suction tube 21 extends from the front surface of the partition plate 11 a height which is almost the same as that of the projections 12. Suction openings 25 are also provided at the top, bottom and left and right sides of the suction tube 21 in lines along the longitudinal direction of the suction tube 21. The top suction openings 25 pass through the back side of the partition plate 11 through the corresponding holes 14 provided on the concave 13 of the partition plate 11, in order to continuously remove liquid on the front surface and the back side portion of the partition plate 11 by the operation of suction pump 33 during the heart operation of the patient. The partition plate 11 may be provided through the tube bottom face, in addition to the tube tip end, the both right, left side faces of the tube, and the tube top portion. Air-tube 23 for introducing air from the outside to the central portion of the partition plate 11 and into the upper surface of the suction tube 21 has an outer diameter of 2 mm and an inner diameter of 1 mm, and is bonded by a bonding agent along the suction tube 21. The air tube is provided to assist the suction operation of the suction tube.

The shape of the partition plate 11 of the present invention is not restricted to an oval as shown in FIG. 1, but may be round or oval with a notch portion 16 rounded off in one portion thereof as shown in FIG. 8 of the third embodiment of the present invention. The reason why such a notch portion 16 as described hereinabove is provided is that it is often convenient to provide an escapement for blood vessels, as in the case of the human heart.

The suction tube 21 of the present invention may be branched into two, three, or more forks each having a suction opening at its tip end. Also, a ready-made spreader set or sucker may be bonded as is.

As is clear from the foregoing description, according to the arrangement of the present invention, numerous types of spreader sets or suckers are not required to be prepared as before and the operators therefor are not required, thus simplifying the heart opening procedure. Also, as the small projections are provided on the surface of the partition plate, the adiabatic property of the mat is improved and the unnecessary fluid flows smoothly into the tube suction openings. Furthermore, the tissues of the heart are raised by projections to prevent the tube suction openings from being blocked, thus allowing normal suction to be performed.

Although the present invention has been fully described in connection with the preferred embodiments thereof with reference to the accompanying drawings, it is to be noted that various changes and modifications are apparent to those skilled in the art. For instance, as shown in FIG. 10 and 11, the mat means 10 may further provide a passage 41 for introducing a medium such as cold water from the outside to the inside of mat means 10 in order to control the surface temperature of the mat means 10. The passage is formed as a kind of cavity 41, as shown in FIG. 11, in molding, and is provided with an outlet and an inlet so as to circulate the medium from the inlet to the outlet through the cavity 41. The outlet is provided with an exhaust pipe 44, one end of which is connected to the cavity and the other end is opened to discharge, while the inlet is provided with an inlet pipe 42, one end of which is connected to the cavity and the other end is connected with a water pump for supplying cold water into the passage. Also, the cavity is provided for almost the entire extent of the mat means. Such changes and modifications are to be understood as included within the scope of the present invention as defined by the appended claims unless they depart therefrom.

What is claimed is:

1. Suction equipment for use in a medical operation, comprising:

a partition plate, said partition plate being formed of a soft, elastically bendable material and having sufficient area to substantially encompass an internal organ and sufficient thickness to allow bending to substantially encompass the organ;

a plurality of projections spaced upon and extending from an upper surface of said partition plate;

passage means including an enclosed cavity extending through the interior of said partition plate;

suction means, including a flexible tube, one end of said flexible tube being mounted on said upper surface of said partition plate, said one end of said flexible tube having at least one opening for the introduction of fluids into said tube, the other end of said flexible tube being adapted for connection to a suction pump; and means for circulating a fluid medium through said passage means to control the temperature of said upper surface of said partition plate.

2. Suction equipment as in claim 1, wherein said means for circulating includes an exit port and an inlet port adapted to be connected with a circulating pump for circulating the medium.

3. Suction equipment for use in a medical operation, comprising:

a partition plate, said partition plate being concavely curved in mutually perpendicular directions and having a front face on the concave surface thereof, said partition plate formed of an abiabatic, soft, elastically bendable material and having sufficient area to substantially encompass an internal organ to be operated on and thickness which is sufficiently small to allow easy bending to substantially encompass the organ to be operated on, whereby the encompassed organ can be subjected to a local low temperature on the front face while the surrounding area on the opposite side from said front face is thermally insulated from the low temperature by said partition plate;

a plurality of projections on said front face spaced from each other and extending outwardly from said front face of said partition plate;

suction means, including a flexible tube, one end of said flexible tube being mounted on said front face of said partition plate between said projections and with said projections closest to said tube being spaced laterally therefrom, said one end of said flexible tube having a laterally of openings therein at least along the opposite lateral sides thereof adjacent said projections for the introduction of fluids into said tube, the other end of said flexible tube being adapted for connection to a suction pump; and auxiliary tube means extending along and attached to said flexible tube and having one end adjacent said openings for introducing air to a location proximate said openings of said flexible tube.

4. Suction equipment as in claim 3, wherein said area of said partition plate is of a substantially round shape, and said one end of said tube is mounted substantially at the center thereof.

5. Suction equipment as in claim 3, wherein each of said projections has a cylindrical dot-shape.

6. Suction equipment as in claim 3, wherein each of said projections extends along said partition plate in a line.

7. Suction equipment as in claim 3, wherein said partition plate is provided with a line of perforations extending therethrough, whereby a portion of the partition plate may be removed to reduce said area of said partition plate.

8. Suction equipment as in claim 3, wherein said partition plate is an integrally molded unit.

9. Suction equipment as claimed in claim 3, wherein said partition plate further includes an extra portion of said sufficient thickness and formed of said material integrally extending from a portion of the periphery of said partition plate a distance greater than the cross-sectional site of said projections, said extra portion being devoid of said projections.

* * * * *